(12) United States Patent
Morita (10) Patent No.: US 11,883,221 B2
(45) Date of Patent: Jan. 30, 2024

(54) IMAGING CONTROL APPARATUS, IMAGING CONTROL METHOD, AND IMAGING CONTROL PROGRAM

(71) Applicant: FUJIFILM CORPORATION, Tokyo (JP)

(72) Inventor: Junya Morita, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 334 days.

(21) Appl. No.: 17/464,717

(22) Filed: Sep. 2, 2021

(65) Prior Publication Data
US 2021/0393225 A1 Dec. 23, 2021

Related U.S. Application Data

(63) Continuation of application No. PCT/JP2019/044391, filed on Nov. 12, 2019.

(30) Foreign Application Priority Data

Mar. 27, 2019 (JP) ................................. 2019-060371

(51) Int. Cl.
*A61B 6/00* (2006.01)
*G06V 10/25* (2022.01)
(Continued)

(52) U.S. Cl.
CPC .............. *A61B 6/502* (2013.01); *A61B 6/025* (2013.01); *A61B 6/466* (2013.01); *A61B 6/469* (2013.01);
(Continued)

(58) Field of Classification Search
CPC ......... A61B 6/502; A61B 6/025; A61B 6/466; A61B 6/469; A61B 6/0414; A61B 6/488;
(Continued)

(56) References Cited

U.S. PATENT DOCUMENTS 8,553,837 B2 * 10/2013 Johansson .............. A61B 6/542
378/22
9,168,013 B2 * 10/2015 Roessl ................... A61B 6/488
(Continued)

FOREIGN PATENT DOCUMENTS

EP 3005298 A1 4/2016
JP 2007-050264 A 3/2007
(Continued)

OTHER PUBLICATIONS

Extended European Search Report dated Apr. 22 , 2022, issued in corresponding EP Patent Application No. 19921770.4.
(Continued)

*Primary Examiner* — Wesley J Tucker
(74) *Attorney, Agent, or Firm* — SOLARIS Intellectual Property Group, PLLC (57) ABSTRACT

An image acquisition unit acquires a first breast image by imaging a breast which is being compressed by first imaging. A three-dimensional information derivation unit derives three-dimensional information of a mammary gland included in the first breast image. An imaging mode setting unit sets an imaging mode for second imaging of the breast based on the three-dimensional information. The image acquisition unit acquires a second breast image by imaging the breast without releasing a state during the first imaging where the breast is compressed by the second imaging based on the set imaging mode.

13 Claims, 8 Drawing Sheets

| THREE-DIMENSIONAL INFORMATION | IMAGING MODE | | |
|---|---|---|---|
| | THICKNESS OF BREAST IS EQUAL TO OR SMALLER THAN Th2 | THICKNESS OF BREAST IS LARGER THAN Th2 | ~LUT2 |
| EQUAL TO OR SMALLER THAN Th1 | SIMPLE IMAGING | COMBINATION IMAGING | |
| LARGER THAN Th1 | TOMOSYNTHESIS IMAGING | COMBINATION IMAGING | |

(51) Int. Cl.
*A61B 6/02* (2006.01)
*G06T 7/00* (2017.01)
(52) U.S. Cl.
CPC ............ *G06T 7/0012* (2013.01); *G06V 10/25* (2022.01); *G06T 2207/30068* (2013.01)
(58) Field of Classification Search
CPC ....... A61B 6/463; A61B 6/545; G06T 7/0012; G06T 2207/30068; G06V 10/25
See application file for complete search history.

(56) References Cited

U.S. PATENT DOCUMENTS

| | | | | |
|---|---|---|---|---|
| 11,529,114 | B2* | 12/2022 | Matsuura | A61B 8/0825 |
| 2007/0036265 | A1 | 2/2007 | Jing et al. | |
| 2007/0242800 | A1 | 10/2007 | Jing et al. | |
| 2008/0249415 | A1* | 10/2008 | Okamura | A61B 8/5207 600/445 |
| 2009/0118614 | A1* | 5/2009 | Sendai | A61B 8/4416 600/425 |
| 2009/0304147 | A1 | 12/2009 | Jing et al. | |
| 2010/0135456 | A1* | 6/2010 | Jing | A61B 6/06 378/22 |
| 2010/0321404 | A1 | 12/2010 | Fischer et al. | |
| 2013/0272494 | A1* | 10/2013 | DeFreitas | A61B 6/025 378/37 |
| 2014/0133626 | A1 | 5/2014 | Jang et al. | |
| 2015/0093013 | A1* | 4/2015 | Morita | G16H 50/20 382/132 |
| 2017/0245818 | A1* | 8/2017 | Smith | G06T 11/006 |
| 2018/0279971 | A1 | 10/2018 | Nishi et al. | |
| 2019/0076108 | A1* | 3/2019 | Machida | G06T 11/008 |
| 2021/0015435 | A1* | 1/2021 | Defreitas | A61B 6/0435 |
| 2021/0259648 | A1* | 8/2021 | Jeanmaire | G06T 7/0016 |
| 2021/0315533 | A1* | 10/2021 | Kim | A61B 6/0435 |

FOREIGN PATENT DOCUMENTS

| | | |
|---|---|---|
| JP | 2009-072410 A | 4/2009 |
| JP | 2012-135444 A | 7/2012 |
| JP | 2014061232 A | 4/2014 |
| JP | 2017047103 A | 3/2017 |
| JP | 2018-166957 A | 11/2018 |

OTHER PUBLICATIONS

International Search Report issued in International Application No. PCT/JP2019/044391 dated Jan. 7, 2020.

Written Opinion of the ISA issued in International Application No. PCT/JP2019/044391 dated Jan. 7, 2020.

English language translation of the following: Office action dated May 17, 2022 from the JPO in a Japanese patent application No. 2021-508713 corresponding to the instant patent application. This office action translation is submitted now in order to supplement the understanding of the cited references which are being disclosed in the instant Information Disclosure Statement.

English language translation of the following: Office action dated Aug. 2, 2022 from the JPO in a Japanese patent application No. 2021-508713 corresponding to the instant patent application. This office action translation is submitted now in order to supplement the understanding of the cited references which are being disclosed in the instant Information Disclosure Statement.

* cited by examiner

| THREE-DIMENSIONAL INFORMATION | IMAGING MODE |
|---|---|
| EQUAL TO OR SMALLER THAN Th1 | SIMPLE IMAGING |
| LARGER THAN Th1 | TOMOSYNTHESIS IMAGING |

LUT1

FIG. 7

| THREE-DIMENSIONAL INFORMATION | IMAGING MODE | |
|---|---|---|
| | THICKNESS OF BREAST IS EQUAL TO OR SMALLER THAN Th2 | THICKNESS OF BREAST IS LARGER THAN Th2 |
| EQUAL TO OR SMALLER THAN Th1 | SIMPLE IMAGING | COMBINATION IMAGING |
| LARGER THAN Th1 | TOMOSYNTHESIS IMAGING | COMBINATION IMAGING |

LUT2

IMAGING CONTROL APPARATUS, IMAGING CONTROL METHOD, AND IMAGING CONTROL PROGRAM

CROSS-REFERENCE TO RELATED APPLICATIONS

The present application is a Continuation of PCT International Application No. PCT/JP2019/044391, filed on Nov. 12, 2019, which claims priority to Japanese Patent Application No. 2019-060371, filed on Mar. 27, 2019. Each application above is hereby expressly incorporated by reference, in its entirety, into the present application.

BACKGROUND

Technical Field

The present disclosure relates to an imaging control apparatus, an imaging control method, and an imaging control program.

Related Art

In recent years, in order to promote early detection of breast cancer, image diagnosis using a radiography apparatus (called mammography) that performs imaging of a breast has attracted attention. In mammography, the breast is placed on an imaging table, and imaging is performed in a state where the breast is being compressed by a compression plate. The breast mainly consists of mammary gland tissue and adipose tissue, and in image diagnosis, it is important to detect a lesion such as a tumor or calcification hidden in the mammary gland tissue. For this reason, a radiographic image (breast image) acquired by imaging the breast using mammography is subjected to image processing by a dedicated operation terminal or the like, and then used for diagnosis by a doctor. The doctor examines the presence or absence of an abnormal portion by reading the breast image displayed on a display.

Here, in the breast, mammary gland tissue and adipose tissue are mixed with each other. In a case of a breast in which a density of mammary gland is high, the abnormal portion may be hidden by the mammary gland in the breast image, and as a result, it may be difficult to find the abnormal portion.

On the other hand, in mammography, there has been proposed tomosynthesis imaging of performing imaging by moving a radiation source and irradiating a breast with radiation at a plurality of radiation source positions, and generating tomographic images in which desired tomographic planes are highlighted by adding a plurality of projection images acquired by the imaging. In the tomosynthesis imaging, the plurality of projection images are acquired by moving the radiation source in parallel with a radiation detector or so as to draw a circular or an elliptical arc according to characteristics of an imaging apparatus and required tomographic images and imaging a breast at the plurality of radiation source positions, and the tomographic images are generated by reconfiguring the projection images using an inverse projection method such as a simple inverse projection method or a filtering inverse projection method.

The tomographic images are generated on a plurality of tomographic planes of the breast, and thus it is possible to separate structures that are overlapped in a depth direction in which the tomographic planes of the breast are lined up. Therefore, it is possible to detect a lesion which is unlikely to be detected in the two-dimensional image (hereinafter, referred to as a simple two-dimensional image) acquired by simple imaging in the related art.

In a case where imaging of a subject is performed by using radiation, in order to prevent a decrease in contrast due to an influence of scattered radiation generated in the subject, a scattered radiation removal grid (hereinafter, simply referred to as a grid) is used. On the other hand, in tomosynthesis imaging, imaging is performed by irradiating the subject with radiation at each of a plurality of radiation source positions. Thus, an angle of incidence of the radiation on a radiation detector differs at each imaging position. For this reason, in a case where imaging is performed using a grid, vignetting in which the radiation is blocked by the grid occurs depending on the radiation source position, and as a result, an amount of the radiation reaching the radiation detector may be reduced. Thus, in a case where tomosynthesis imaging is performed, the grid is not used.

On the other hand, in a case where the grid is not used, a noise in the projection image and even the tomographic image is increased due to an influence of the scattered radiation, and as a result, an image quality is deteriorated. In particular, in a case of a patient with a thick breast, a degree of scattering of the radiation is increased, and this causes an increase of a noise caused by the scattered radiation. As a result, even though tomosynthesis imaging is performed, it may be more difficult to detect an abnormal portion as compared with a simple two-dimensional image.

For this reason, in mammography, a method of performing both tomosynthesis imaging and simple imaging has been proposed (refer to JP2007-50264A). However, in a case where both tomosynthesis imaging and simple imaging are performed, an exposure dose to the subject increases. In order to solve the problem, there is proposed a method of calculating a density of mammary gland of a breast using a breast image acquired in the past and switching an imaging mode between simple imaging and tomosynthesis imaging according to the density of mammary gland (refer to JP2012-135444A). Specifically, in the method described in JP2012-135444A, as the density of mammary gland increases, the imaging mode is switched such that tomosynthesis imaging is performed. In JP2012-135444A, in an entire region of the breast image or in a predetermined region of the breast image, pixels having a relatively low density are considered as pixels of mammary gland, and in an entire region of the breast image or in a predetermined region of the breast image, a ratio of an area of a mammary gland region is calculated as an amount of mammary gland.

Figure 11:
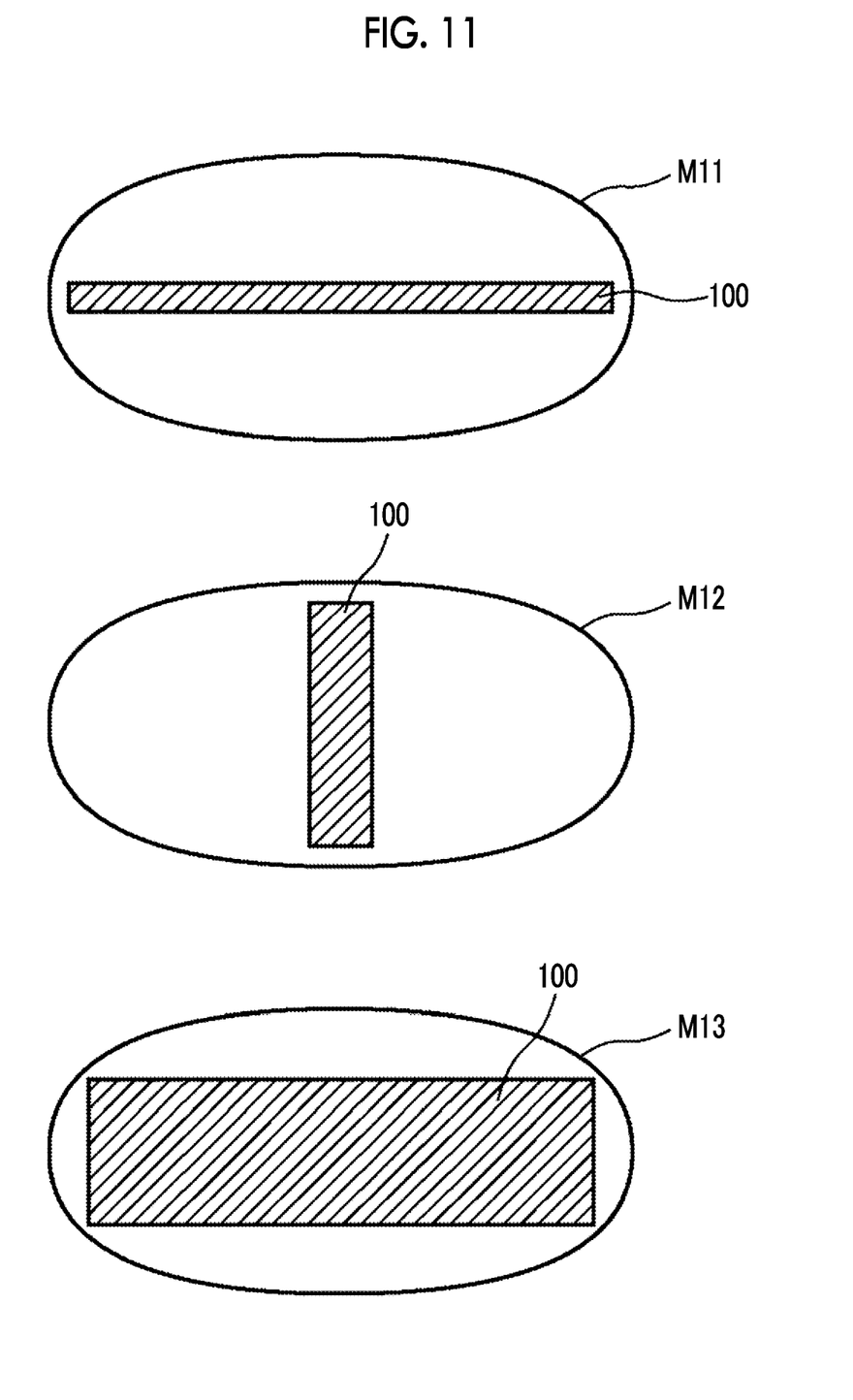
FIG. 11 is a diagram for explaining a thickness of a mammary gland in the breast.

However, as described in JP2012-135444A, in the method based on the ratio of the area of the mammary gland region, an appropriate imaging mode may not be selected. For example, as illustrated in the breast M11 of FIG. 11, in a case where the mammary gland 100 is thin and widely distributed in the breast, in the method described in JP2012-135444A, the ratio of the area of the mammary gland is large, and thus tomosynthesis imaging is selected as the imaging mode. However, as compared to a case where the mammary gland 100 is also distributed in a thickness direction of the breast as in a case of the breast M12 or the breast M13 illustrated in FIG. 11, the breast M11 has a small advantage of tomosynthesis imaging, which can separate overlapping of the breast in the thickness direction. The tomosynthesis imaging is performed multiple times in a state where the breast is being compressed. For this reason, in a case of the breast M11 as illustrated in FIG. 11, in a case where simple imaging is performed, a burden on the patient and an exposure dose to the patient decrease.

SUMMARY OF THE INVENTION

The present disclosure has been made in view of the above circumstances, and an object of the present disclosure is to make it possible to appropriately set an imaging mode of a breast.

According to an aspect of the present disclosure, there is provided an imaging control apparatus including: an image acquisition unit that acquires a first breast image by imaging a breast which is being compressed by first imaging; a three-dimensional information derivation unit that derives three-dimensional information of a mammary gland included in the first breast image; and an imaging mode setting unit that sets an imaging mode for second imaging of the breast based on the three-dimensional information, in which the image acquisition unit acquires a second breast image by imaging the breast without releasing a state during the first imaging where the breast is compressed by the second imaging based on the set imaging mode.

In the imaging control apparatus according to the present disclosure, the three-dimensional information derivation unit may derive, as the three-dimensional information, any of a volume of the mammary gland, a ratio of the volume of the mammary gland, or a thickness of the mammary gland in an interest region of the breast.

Further, in the imaging control apparatus according to the present disclosure, the interest region may be an entire region of the breast.

Further, in the imaging control apparatus according to the present disclosure, the interest region may be a region in which the mammary gland exists in a predetermined ratio or more with respect to a thickness of the breast.

Further, in the imaging control apparatus according to the present disclosure, the imaging mode setting unit may set, as the imaging mode, any of simple two-dimensional imaging, tomosynthesis imaging, and combination imaging of simple imaging and tomosynthesis imaging based on the three-dimensional information.

Further, in the imaging control apparatus according to the present disclosure, the imaging mode setting unit may set the imaging mode based on a thickness of the breast.

Further, in the imaging control apparatus according to the present disclosure, the imaging mode setting unit may set the imaging mode to the simple two-dimensional imaging in a case where the volume of the mammary gland or the ratio of the volume of the mammary gland is equal to or smaller than a predetermined threshold value, and may set the imaging mode to the tomosynthesis imaging in a case where the volume of the mammary gland or the ratio of the volume of the mammary gland is larger than the threshold value.

In this case, the threshold value may be experimentally set as appropriate according to the volume of the mammary gland or the ratio of the volume of the mammary gland.

Further, in the imaging control apparatus according to the present disclosure, the imaging mode setting unit may set the imaging mode to the simple two-dimensional imaging in a case where the volume of the mammary gland or the ratio of the volume of the mammary gland is equal to or smaller than a predetermined first threshold value and the thickness of the breast is equal to or smaller than a predetermined second threshold value, may set the imaging mode to the tomosynthesis imaging in a case where the volume of the mammary gland or the ratio of the volume of the mammary gland is larger than the first threshold value and the thickness of the breast is equal to or smaller than the second threshold value, and may set the imaging mode to the combination imaging in a case where the thickness of the breast is larger than the second threshold value.

In this case, the first threshold value may be experimentally set as appropriate according to the volume of the mammary gland or the ratio of the volume of the mammary gland. Further, the second threshold value may be experimentally set as appropriate according to the thickness of the breast.

Further, in the imaging control apparatus according to the present disclosure, the imaging mode setting unit may set the imaging mode to the simple two-dimensional imaging in a case where the thickness of the mammary gland is equal to or smaller than a predetermined threshold value, and may set the imaging mode to the tomosynthesis imaging in a case where the thickness of the mammary gland is larger than the threshold value.

In this case, the threshold value may be experimentally set as appropriate according to the thickness of the mammary gland.

Further, in the imaging control apparatus according to the present disclosure, the imaging mode setting unit may set the imaging mode to the simple two-dimensional imaging in a case where the thickness of the mammary gland is equal to or smaller than a predetermined third threshold value and the thickness of the breast is equal to or smaller than a predetermined fourth threshold value, may set the imaging mode to the tomosynthesis imaging in a case where the thickness of the mammary gland is larger than the third threshold value and the thickness of the breast is equal to or smaller than the fourth threshold value, and may set the imaging mode to the combination imaging in a case where the thickness of the breast is larger than the fourth threshold value.

In this case, the third threshold value may be experimentally set as appropriate according to the thickness of the mammary gland. Further, the fourth threshold value may be experimentally set as appropriate according to the thickness of the breast.

Further, the imaging control apparatus according to the present disclosure may further include a notification unit that notifies at least one of the set imaging mode or a remaining time of the second imaging by the imaging mode.

According to another aspect of the present disclosure, there is provided an imaging control method including: acquiring a first breast image by imaging a breast which is being compressed by first imaging; deriving three-dimensional information of a mammary gland included in the first breast image; setting an imaging mode for second imaging of the breast based on the three-dimensional information; and acquiring a second breast image by imaging the breast without releasing a state during the first imaging where the breast is compressed by the second imaging based on the set imaging mode.

A program causing a computer to execute the imaging control method according to the aspect of the present disclosure may be provided.

According to still another aspect of the present disclosure, there is provided an imaging control apparatus including: a memory that stores a command to be executed by a computer; and a processor configured to execute the stored command, in which the processor is configured to execute processing of acquiring a first breast image by imaging a breast which is being compressed by first imaging, deriving three-dimensional information of a mammary gland included in the first breast image, setting an imaging mode for second imaging of the breast based on the three-dimensional information, and acquiring a second breast image by imaging the breast without releasing a state during the first imaging where the breast is compressed by the second imaging based on the set imaging mode.

According to the present disclosure, it is possible to appropriately set the imaging mode of the breast.

DETAILED DESCRIPTION

Figure 1:
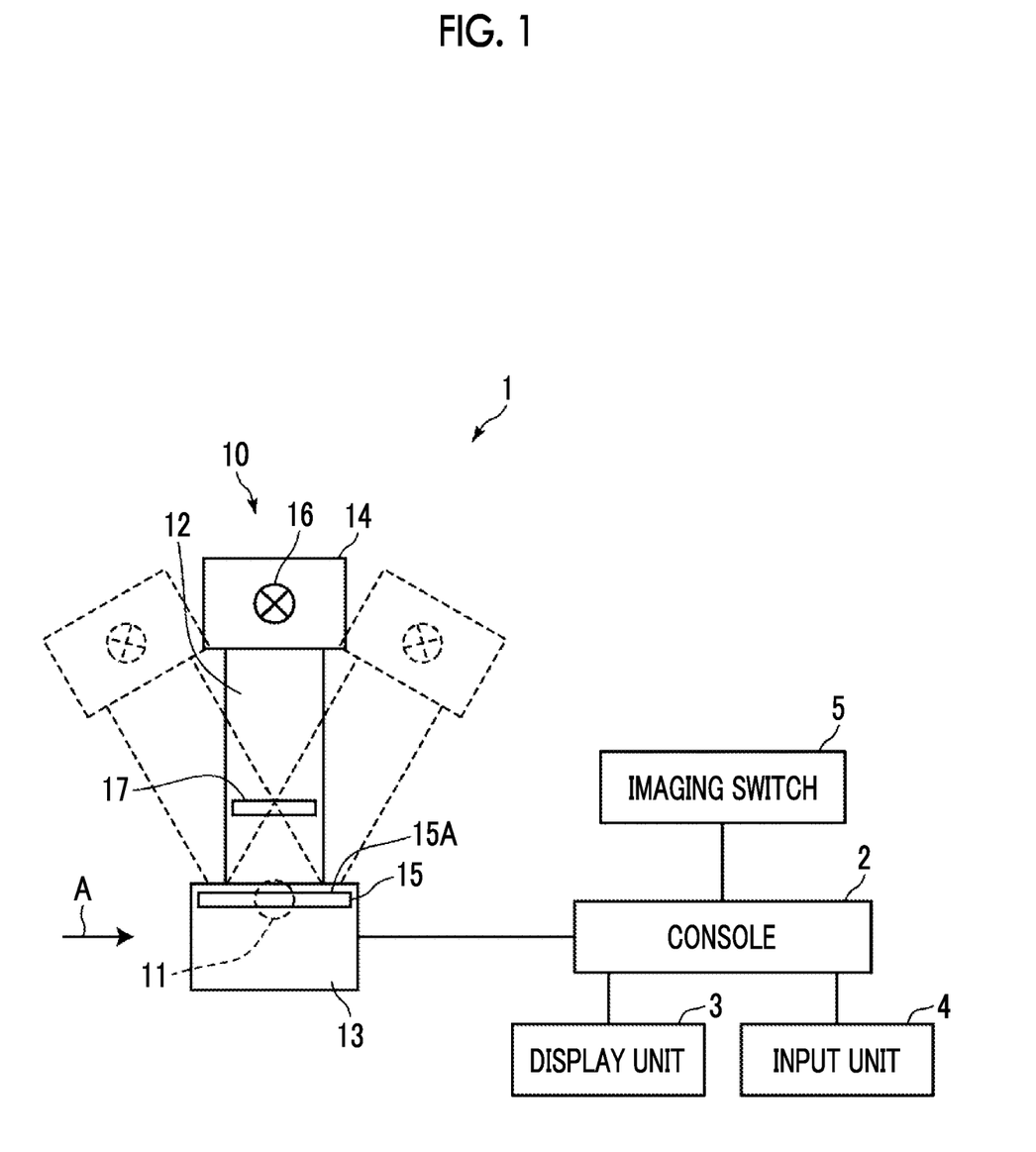
FIG. 1 is a schematic configuration diagram of a radiography system to which an imaging control apparatus according to an embodiment of the present disclosure is applied.
Figure 2:
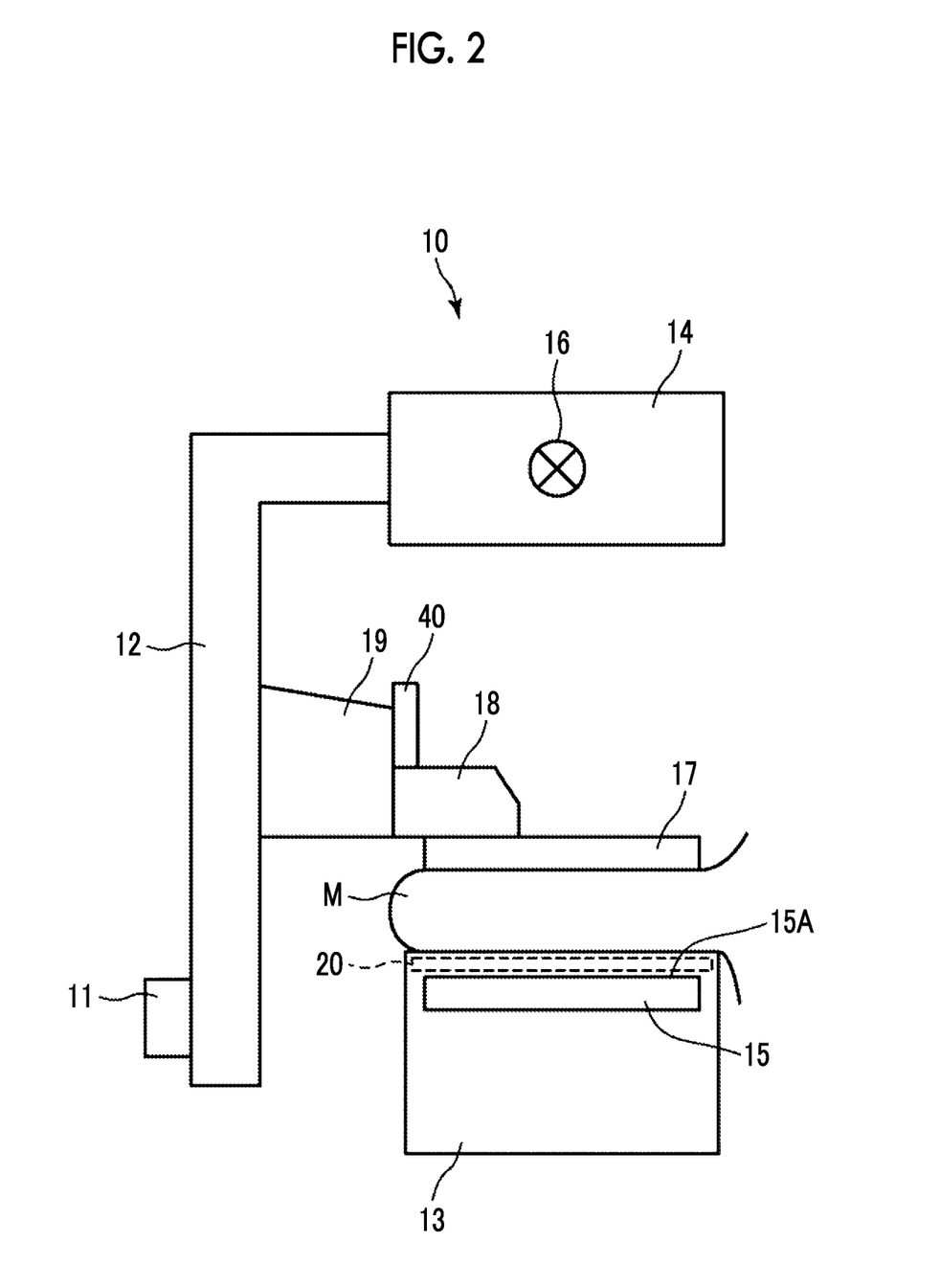
FIG. 2 is a diagram illustrating a mammography apparatus as viewed from a direction of an arrow A in FIG. 1.

Hereinafter, embodiments of the present disclosure will be described with reference to the drawings. FIG. 1 is a schematic configuration diagram of a radiography system to which an imaging control apparatus according to an embodiment of the present disclosure is applied, and FIG. 2 is a diagram illustrating a mammography apparatus included in the radiography system as viewed from a direction of an arrow A in FIG. 1.

As illustrated in FIG. 1, a radiography system 1 according to the present embodiment includes a console 2 and a mammography apparatus 10. The console 2 includes a display unit 3, an input unit 4, and an imaging switch 5.

The radiography system 1 according to the present embodiment has a function of performing tomosynthesis imaging of a patient's breast by the mammography apparatus 10 and acquiring tomographic images of the breast on a plurality of tomographic planes, based on an instruction (imaging order) which is input from an external system (for example, a radiology information system (RIS)) via the console 2, in response to an operation of an operator such as a doctor or a radiologist. In the present embodiment, the mammography apparatus 10 can generate a tomographic breast image and a two-dimensional breast image by performing both tomosynthesis imaging and simple imaging. The two-dimensional breast image means a breast image acquired by simple imaging.

The mammography apparatus 10 includes an arm portion 12 that is connected to a base (not illustrated) by a rotation shaft 11. An imaging table 13 is attached to one end of the arm portion 12, and a radiation irradiation unit 14 is attached to the other end of the arm portion 12 so as to face the imaging table 13. The arm portion 12 is configured such that only the end to which the radiation irradiation unit 14 is attached can be rotated. Therefore, the imaging table 13 is fixed and only the radiation irradiation unit 14 can be rotated. The rotation of the arm portion 12 is controlled by the console 2.

A radiation detector 15, such as a flat panel detector, is provided in the imaging table 13. The radiation detector 15 has a radiation detection surface 15A. In addition, a circuit board including a charge amplifier that converts a charge signal read from the radiation detector 15 into a voltage signal, a sampling two correlation pile circuit that samples the voltage signal output from the charge amplifier, and an analog-to-digital (AD) conversion unit that converts the voltage signal into a digital signal is provided in the imaging table 13. Further, in the present embodiment, the radiation detector 15 is used. On the other hand, the present embodiment is not limited to the radiation detector 15 as long as radiation can be detected and the radiation can be converted into an image.

In the imaging table 13, a scattered radiation removal grid 20 is disposed so as to be inserted and removed between a front surface of the imaging table 13 and the radiation detector 15.

The radiation detector 15 can repeatedly perform recording and reading of a radiographic image, may be a so-called direct-type radiation detector that directly converts radiation such as X-rays into charges, or may be a so-called indirect-type radiation detector that converts radiation such as X-rays into visible light once and converts the visible light into a charge signal. As a method for reading a radiographic image signal, it is desirable to use the following method: a so-called thin film transistor (TFT) reading method which reads a radiographic image signal by turning on and off a TFT switch; or a so-called optical reading method which reads a radiographic image signal by irradiating a target with read light. On the other hand, the reading method is not limited thereto, and other methods may be used.

A radiation source 16 is accommodated in the radiation irradiation unit 14. The radiation source 16 emits X-rays as radiation. The console 2 controls a timing when the radiation source 16 emits the radiation and radiation generation conditions of the radiation source 16, that is, selection of a target and filter materials, a tube voltage, an irradiation time, and the like.

Further, the arm portion 12 is provided with a compression plate 17 that is disposed above the imaging table 13 and presses and compresses the breast M, a support portion 18 that supports the compression plate 17, and a movement mechanism 19 that moves the support portion 18 in a vertical direction in FIG. 1 and FIG. 2. A distance between the compression plate 17 and the imaging table 13, that is, a compression thickness is input to the console 2. Further, the movement mechanism 19 is provided with a display unit 40 such as a liquid crystal display for displaying various information for a patient. The display unit 40 displays a notification such as a remaining time until the end of imaging, which will be described. The display unit 40 may include a speaker that outputs sound.

The display unit 3 is a display device such as a cathode ray tube (CRT) or a liquid crystal display, and displays a first breast image and a second breast image, which are acquired as described later, and messages required for operations. The display unit 3 may include a speaker that outputs sound.

The input unit 4 includes a keyboard, a mouse, and a touch-panel-type input device, and receives inputs to operate the mammography apparatus 10 from the operator. Further, the input unit 4 receives an input of various kinds of information required for imaging, such as an imaging condition, and an instruction to correct information. In the present embodiment, each unit of the mammography apparatus 10 is operated according to the information which is input from the input unit 4 by the operator.

The imaging switch 5 is provided from a viewpoint of safety. Only a period for which the operator presses the imaging switch 5, a series of imaging including irradiation of radiation is executed, and imaging is stopped when the operator releases the imaging switch 5.

An imaging control program according to the present embodiment is installed on the console 2. In the present embodiment, the console 2 may be a workstation or a personal computer that is directly operated by the operator, or may be a server computer that is connected to the mammography apparatus 10 via a network. The imaging control program is distributed by being recorded on a recording medium such as a digital versatile disc (DVD) or a compact disc read only memory (CD-ROM), and is installed in a computer from the recording medium. Alternatively, the imaging control program is stored in a storage device of a server computer connected to the network or a network storage in a state where an access from the outside is allowed, and is downloaded and installed in the computer as required.

Figure 3:
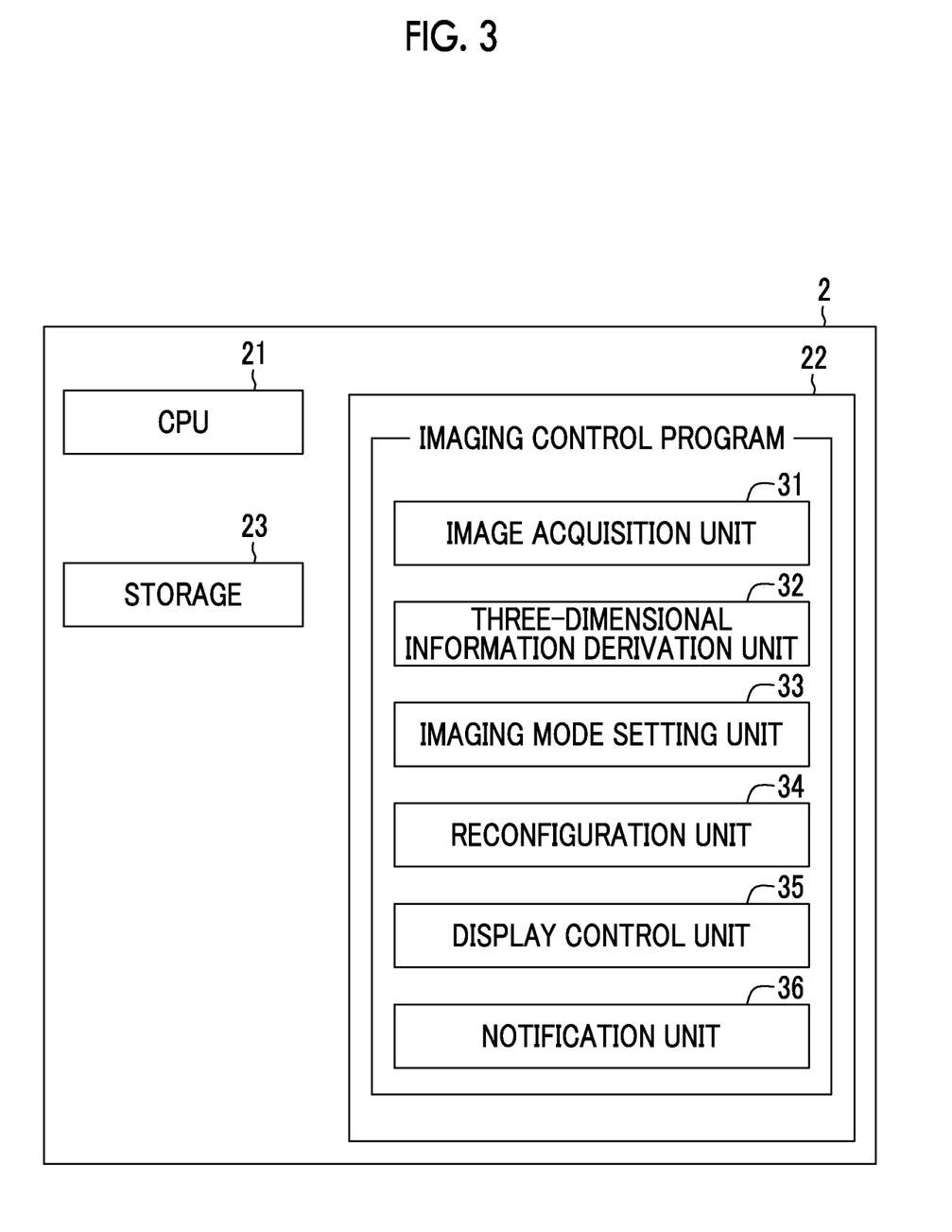
FIG. 3 is a diagram illustrating a schematic configuration of the imaging control apparatus realized by installing, in a computer as a console, an imaging control program according to the present embodiment.

FIG. 3 is a diagram illustrating a schematic configuration of the imaging control apparatus realized by installing, on the console 2, the imaging control program according to the present embodiment. As illustrated in FIG. 3, the imaging control apparatus includes, as a standard computer configuration, a central processing unit (CPU) 21, a memory 22, and a storage 23.

The storage 23 is a storage device such as a hard disk drive or a solid state drive (SSD), and stores various kinds of information including the imaging control program for driving each unit of the mammography apparatus 10. The first breast image acquired by first imaging and the second breast image acquired by second imaging are also stored.

The memory 22 temporarily stores the programs, which are stored in the storage 23, in order to cause the CPU 21 to execute various processing. The imaging control program defines, as processing to be executed by the CPU 21, image acquisition processing of acquiring a first breast image and a second breast image by causing the mammography apparatus 10 to perform the first imaging and the second imaging to be described, three-dimensional information derivation processing of deriving three-dimensional information of a mammary gland included in the first breast image acquired by the first imaging, imaging mode setting processing of setting an imaging mode for the second imaging of the breast M based on the three-dimensional information, reconfiguration processing of generating a plurality of tomographic images at each of the plurality of tomographic planes of the breast M by reconfiguring the plurality of acquired projection images in a case where the imaging mode of the second imaging is tomosynthesis imaging, display control processing of displaying the second breast image acquired by imaging on the display unit 3, and notification processing of notifying the operator of at least one of the set imaging mode or the remaining time of the second imaging according to the imaging mode.

The CPU 21 executes pieces of the processing according to the imaging control program, and thus the computer including the console 2 functions as an image acquisition unit 31, a three-dimensional information derivation unit 32, an imaging mode setting unit 33, a reconfiguration unit 34, a display control unit 35, and a notification unit 36.

The image acquisition unit 31 causes the mammography apparatus 10 to perform pre-imaging as the first imaging, in order to optimize an imaging condition of the second imaging and to set the imaging mode to be described. The pre-imaging is imaging of irradiating the breast M with a low dose of radiation according to an imaging condition of the pre-imaging to be described. The breast image acquired by the first imaging is referred to as the first breast image.

The first breast image may be displayed on the display unit 3 by the display control unit 35. In this case, the operator can determine whether or not positioning of the breast M is appropriate based on the displayed first breast image. In a case where it is determined that positioning of the breast M is appropriate, the second imaging to be described is performed. In a case where it is determined that positioning of the breast M is not appropriate, the imaging switch 5 to be described is released, positioning of the breast M is performed again, and the first imaging is performed again.

Further, the image acquisition unit 31 acquires a second breast image by imaging the breast with the same positioning as positioning of the first imaging by the second imaging based on the imaging mode which is set by the imaging mode setting unit 33 as will be described. Here, examples of the second imaging include simple imaging, tomosynthesis imaging, and combination imaging of simple imaging and tomosynthesis imaging (hereinafter, simply referred to as combination imaging). The types of imaging are set as imaging modes by the imaging mode setting unit 33. The imaging of the breast with the same positioning means that the first imaging and the second imaging are performed without releasing a state where the breast M is compressed by the compression plate 17 and positioned.

In a case where the image acquisition unit 31 causes the mammography apparatus 10 to perform tomosynthesis imaging, the image acquisition unit 31 acquires a plurality of projection images Gi (i=1 to n, where n is the number of radiation source positions and is, for example, n=15) at a plurality of radiation source positions by moving the radiation source 16 by rotating the arm portion 12 of the mammography apparatus 10 around the rotation shaft 11, irradiating the breast M with radiation at a plurality of radiation source positions obtained by the movement of the radiation source 16 according to a predetermined first imaging condition for tomosynthesis imaging, and detecting the radiation passing through the breast M by the radiation detector 15.

Figure 4:
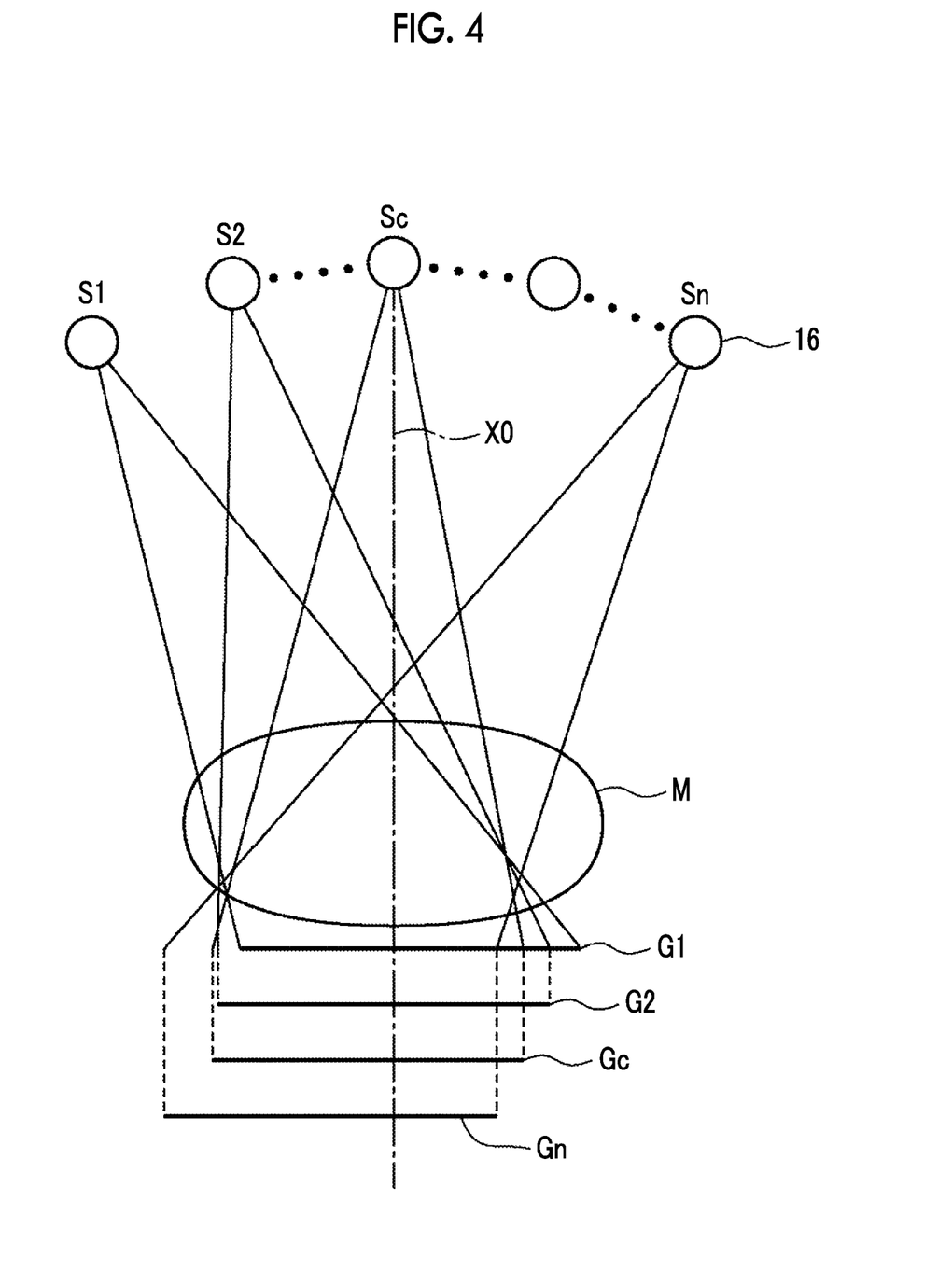
FIG. 4 is a diagram for explaining tomosynthesis imaging.

FIG. 4 is a diagram for explaining the acquisition of the projection images Gi. As illustrated in FIG. 4, the radiation source 16 is moved to each of radiation source positions S1, S2, ..., and Sn. The radiation source 16 drives and irradiates the breast M with radiation at each of the radiation source positions. The radiation detector 15 detects X-rays passing through the breast M, and thus the projection images G1, G2, ..., and Gn corresponding to the radiation source positions S1 to Sn are acquired. At each of the radiation source positions S1 to Sn, the breast M is irradiated with the same dose of radiation. The plurality of acquired projection images Gi are stored in the storage 23. In the present embodiment, in a case where tomosynthesis imaging or combination imaging is performed, the image acquisition unit 31 acquires, as a second breast image, a plurality of tomographic images generated from the plurality of projection images Gi by the reconfiguration unit 34 to be described.

The radiation source position Sc illustrated in FIG. 4 is a radiation source position at which the optical axis X0 of the radiation emitted from the radiation source 16 is orthogonal to the detection surface 15A of the radiation detector 15. The radiation source position Sc is referred to as a reference radiation source position Sc.

In a case where the image acquisition unit 31 causes the mammography apparatus 10 to perform simple imaging, the image acquisition unit 31 moves the radiation source 16 to the reference radiation source position Sc by rotating the arm portion 12 of the mammography apparatus 10 around the rotation shaft 11. The image acquisition unit 31 acquires, as a second breast image, a simple two-dimensional image of the breast M by irradiating the breast M with radiation under a predetermined second imaging condition for simple imaging and detecting the radiation passing through the breast M by the radiation detector 15.

In a case where the image acquisition unit 31 causes the mammography apparatus 10 to perform the first imaging, similar to the case of the simple imaging, the image acquisition unit 31 moves the radiation source 16 to the reference radiation source position Sc by rotating the arm portion 12 of the mammography apparatus 10 around the rotation shaft 11. The first imaging may be performed by moving the radiation source 16 to the radiation source position S1.

Hereinafter, the first imaging condition and the second imaging condition will be described. The radiation source 16 includes a filament that outputs electron beams, a target that generates X-rays by collision with the electron beams, and a filter that adjusts energy spectra of the X-rays. The target includes a plurality of different anodic materials such as molybdenum (Mo), rhodium (Rh), and tungsten (W), which are disposed in a selectable state. The filter includes a plurality of different materials, such as molybdenum (Mo), rhodium (Rh), tungsten (W), and aluminum (Al), which are disposed in a selectable state.

The imaging condition is a condition for acquiring an appropriate radiographic image by adjusting the energy spectra (radiation quality) of the radiation with which the breast M is irradiated, and includes, for example, a type of the target of the radiation source 16, a type of the filter of the radiation source 16, and a grid condition indicating the presence or absence of a scattered radiation removal grid. Further, a radiation generation condition for a tube voltage, which is applied between the filament and the target, and an mAs value (tube current×radiation irradiation time) are also included in the imaging condition.

In the present embodiment, a table of the imaging condition of each of tomosynthesis imaging and simple imaging is stored in the storage 23. For example, in the table, the type of the target, the type of the filter, the tube voltage, the mAs value, and the presence or absence of the grid are set according to the thickness of the breast M. Specifically, in tomosynthesis imaging, W/Al for the target and the filter (target is W and filter is Al) and the absence of the grid are set as the first imaging condition. The tube voltage and the mAs value are set according to the thickness of the breast M.

Further, in simple imaging, W/Rh for the target and the filter (target is W and filter is Rh) and the presence of the grid are set as the second imaging condition. The tube voltage and the mAs value are set according to the thickness of the breast M. Therefore, in a case where simple imaging is performed, as illustrated in FIG. 2, the scattered radiation removal grid 20 is inserted between the breast M and the radiation detector 15 in the imaging table 13.

In the present embodiment, an imaging condition of pre-imaging, that is, an imaging condition at the time of the first imaging is also stored in the storage 23. In a state where the position of the radiation source 16 is at the reference radiation source position Sc, in a case where the first imaging is performed, for the target, the filter, and the grid, the imaging condition of the first imaging is the same as the second imaging condition of simple imaging. On the other hand, for the tube voltage and the mAs value, the imaging condition of the first imaging is set to a value smaller than a value in the second imaging condition. Further, in a state where the position of the radiation source 16 is at the radiation source position S1, that is, at a start position of tomosynthesis imaging, in a case where the first imaging is performed, for the target, the filter, and the grid, the imaging condition of the first imaging is the same as the first imaging condition of tomosynthesis imaging. On the other hand, for the tube voltage and the mAs value, the imaging condition of the first imaging is set to a value smaller than a value in the first imaging condition.

Further, in the present embodiment, the imaging condition of the second imaging is optimized based on the first breast image acquired by the first imaging. As the optimization method, for example, a method described in JP2007-236804A or JP2017-51752A may be used. The method described in JP2007-236804A is a method for optimizing the imaging condition of the second imaging based on the first breast image such that a density of a mammary gland region in the radiographic image or the tomographic image acquired by the second imaging is appropriate. The method described in JP2017-51752A is a method for optimizing the imaging condition of the second imaging according to the presence or absence of an implant by determining the presence or absence of the implant in the breast M based on the first breast image.

The three-dimensional information derivation unit 32 acquires three-dimensional information of the mammary gland included in the first breast image acquired by the first imaging. Thus, the three-dimensional information derivation unit 32 first derives a ratio of the mammary gland for each pixel in the breast M included in the first breast image, that is, the mammary gland content ratio. As a method for deriving the mammary gland content ratio, for example, a method described in JP2015-253245A may be used. The method described in JP2015-253245A is a method of creating, from the breast image, an adipose image having a pixel value in a case where all mammary gland tissue of the breast is replaced with adipose tissue and deriving a mammary gland content ratio G(x, y) for each pixel of the breast image by the following Equation (1) based on a pixel value I(x, y) of the breast image, an estimated pixel value A(x, y) of the adipose image, a pixel value IO of a void region in which the radiation directly reaches the radiation detector 15 without passing through the breast M in the breast image, and a value μ which represents a ratio of a radiation attenuation coefficient by the adipose tissue to a radiation attenuation coefficient by the mammary gland. Here, it is assumed that the mammary gland content ratio G(x, y) for each pixel of the entire region of the breast M included in the first breast image is derived.

$$G(x, y) = \frac{A(x, y) - I(x, y)}{I_0 - A(x, y)} \times \frac{1}{\mu - 1} \quad (1)$$

The three-dimensional information derivation unit 32 derives a thickness T(x, y) of the mammary gland for each pixel of the entire region of the breast M included in the first breast image MG1 by multiplying the mammary gland content ratio G(x, y) by the thickness of the breast M. As the thickness of the breast M, the compression thickness of the breast M by the compression plate 17 is used. Further, the thickness of the breast M near a skin line that is not in contact with the compression plate 17 may be derived from a compression thickness of the breast M in a case where a contour of a cross section of the breast M in the thickness direction is regarded as an arc.

Further, the three-dimensional information derivation unit 32 derives, as three-dimensional information of the mammary gland, a volume V0 of the mammary gland by multiplying the derived thickness T(x, y) of the mammary gland by an area of the entire region of the breast M included in the first breast image MG1. As the three-dimensional information, a ratio R0 of the volume of the mammary gland may be derived by dividing the volume V0 of the mammary gland included in the breast M by a volume of the breast M. The volume of the breast M may be derived by multiplying the area of the entire region of the breast M included in the first breast image MG1 by the thickness of the breast M. Further, a representative value T0 of the thickness T(x, y) of the mammary gland (hereinafter, referred to as a representative thickness value) may be used as the three-dimensional information. As the representative thickness value T0, any one of a maximum value, an average value, or a median value of the thickness T(x, y) of the mammary gland may be used. The representative thickness value T0 corresponds to the thickness of the mammary gland according to the present disclosure.

Figure 5:
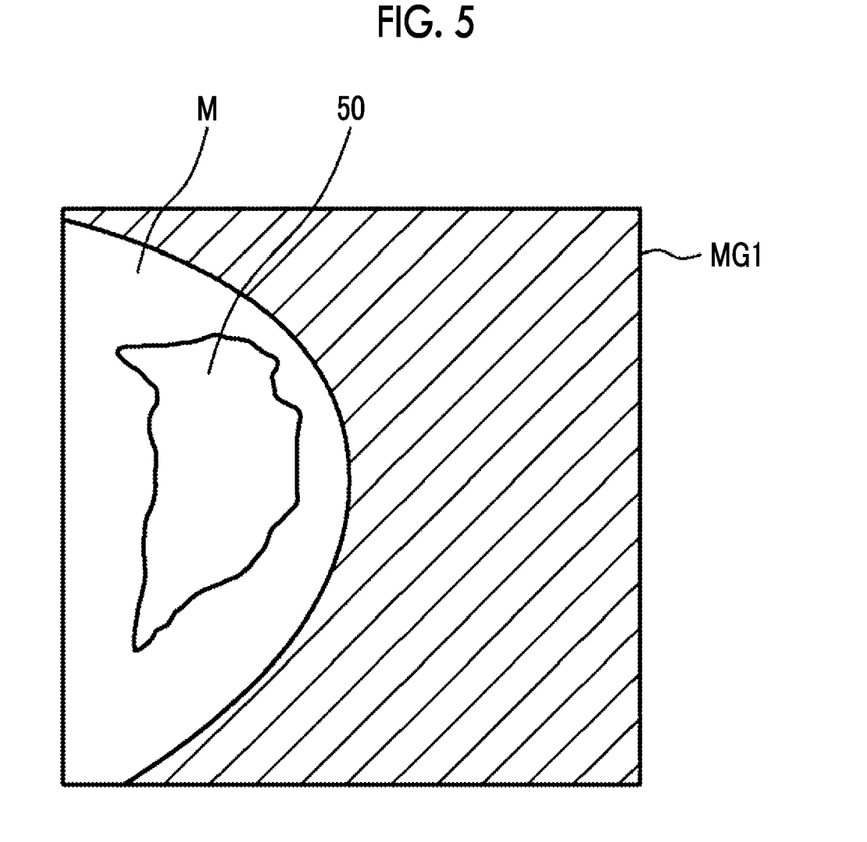
FIG. 5 is a diagram for explaining setting of an interest region of a first breast image.

In the embodiment, the three-dimensional information of the mammary gland for the entire region of the breast M of the first breast image is derived. On the other hand, the present disclosure is not limited thereto. As illustrated in FIG. 5, in the first breast image MG1, a region in which the mammary gland content ratio G(x, y) is equal to or higher than a predetermined value (for example, 10%) is set as an interest region 50, and the thickness T(x, y) of the mammary gland in the interest region 50 is derived. Thereby, a volume V1 of the mammary gland in the interest region 50, a ratio R1 of the volume of the mammary gland, or a representative thickness value T1 may be derived as the three-dimensional information. The volume V1 of the mammary gland in the interest region 50 may be derived by multiplying the area of the interest region 50 by the thickness T(x, y) of the mammary gland in the interest region 50. The ratio R1 of the volume of the mammary gland in the interest region 50 may be derived by dividing the volume V1 of the mammary gland in the interest region 50 by the volume of the breast M in the interest region 50. The volume of the breast M in the interest region 50 may be derived by multiplying the area of the breast M in the interest region 50 of the first breast image MG1 by the thickness of the breast M.

As described above, by deriving the three-dimensional information for the interest region 50, the imaging mode to be described can be set in consideration of a local mass of the mammary gland.

The ratio R0 of the volume of the mammary gland may also be derived using the following Equation (2) described in JP2015-253245A.

$$\frac{\Sigma\, G(x,\, y)*(I_0 - A(x,\, y))}{\Sigma(I_0 - A(x,\, y))} \quad (2)$$

Further, a method of deriving the three-dimensional information of the mammary gland is not limited to the method described in JP2015-253245A, and any method may be used. For example, a method described in a literature "Robust Breast composition Measurement-Volpara, by Ralph Highnam et al., IWDM2010, LNCS; 6136:342-349, 2010" may be used. In the method described in the literature by Highnam et al., assuming that the thickness of the mammary gland is T(x, y), a pixel value of each pixel of the breast image is I(x, y), a pixel value at a pixel position at which the radiation passes through only the adipose tissue is If, the radiation attenuation coefficient of the adipose tissue is μf, and the radiation attenuation coefficient of the mammary gland is μd, the thickness of the mammary gland is derived by the following Equation (3).

$$T(x,y)=(\ln(I(x,y)/If))/(\mu f - \mu d) \quad (3)$$

By the method described in the literature by Highnam et al., in the entire region of the breast M included in the first breast image MG1, the thickness T(x, y) of the mammary gland is derived, and thus, as three-dimensional information of the mammary gland, a volume V0 of the mammary gland included in the breast M can be derived by multiplying the derived thickness T(x, y) of the mammary gland by the area of the breast M included in the first breast image MG1. Further, as the three-dimensional information, a ratio R0 of the volume of the mammary gland can be derived by dividing the volume V0 of the mammary gland included in the breast M by a volume of the breast M.

Further, in the method described in the literature by Highnam et al., a region in which the thickness of the mammary gland is equal to or larger than a predetermined value may be set as an interest region, and the three-dimensional information may be derived only within the interest region.

Figure 6:
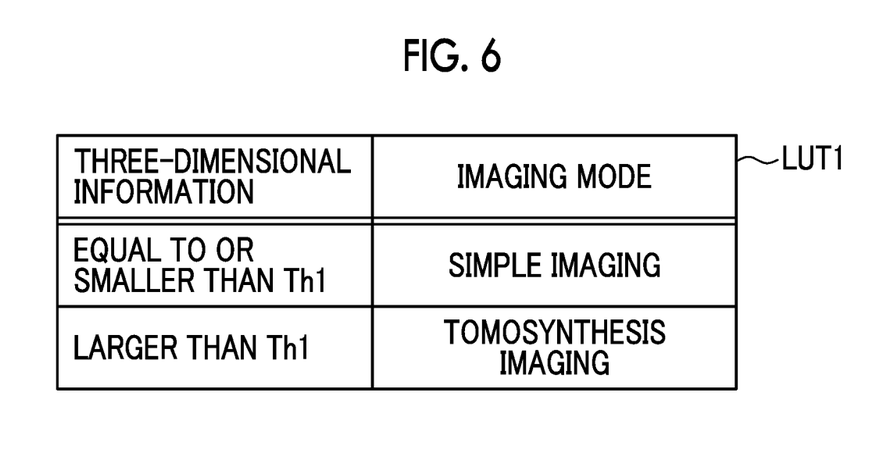
FIG. 6 is a diagram illustrating a table indicating a relationship in which three-dimensional information and an imaging mode are associated with each other.

The imaging mode setting unit 33 sets an imaging mode for the second imaging of the breast M based on the three-dimensional information. In the present embodiment, the storage 23 stores a table indicating a relationship in which the three-dimensional information and the imaging mode are associated with each other. FIG. 6 is a diagram illustrating a table indicating a relationship in which the three-dimensional information and the imaging mode are associated with each other. Here, as the volume of the mammary gland increases, a lesion overlaps with the mammary gland. As a result, it becomes difficult to detect the lesion by simple imaging. Therefore, as illustrated in FIG. 6, in the table LUT1, the three-dimensional information which is equal to or smaller than a first threshold value Th1 is associated with simple imaging, and the three-dimensional information which is larger than the first threshold value Th1 is associated with tomosynthesis imaging.

In FIG. 6, the volumes V0 and V1 of the mammary gland, the ratios R0 and R1 of the volumes of the mammary gland, and the representative thickness values T0 and T1 are collectively illustrated as the three-dimensional information. On the other hand, actually, a table is prepared according to a type of the three-dimensional information derived by the three-dimensional information derivation unit 32. Further, in the table, the first threshold value Th1 is set according to the type of the three-dimensional information to be derived. That is, different first threshold values Th1 are set according to the volumes V0 and V1 of the mammary gland, the ratios R0 and R1 of the volumes of the mammary gland, and the representative thickness values T0 and T1.

Figure 7:
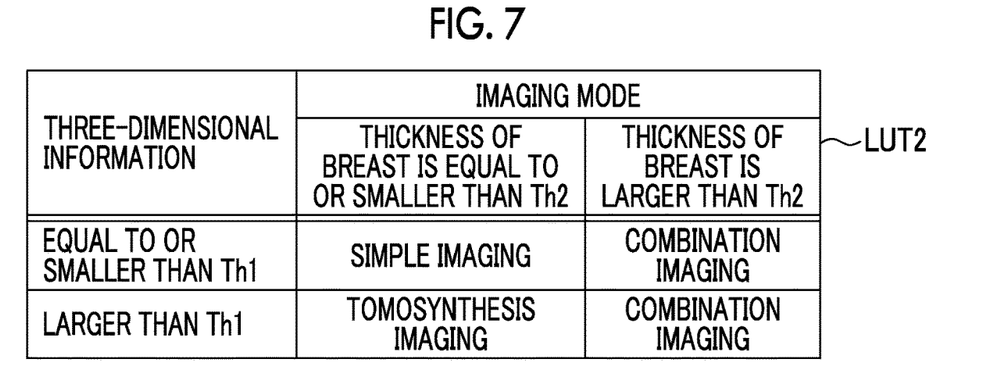
FIG. 7 is a diagram illustrating a table indicating a relationship in which the three-dimensional information and the imaging mode according to a thickness of a breast are associated with each other.

The imaging mode setting unit 33 may set the imaging mode using the thickness of the breast M in addition to the three-dimensional information. In this case, the storage 23 may store a table indicating a relationship in which the three-dimensional information and the imaging mode according to the thickness of the breast M are associated with each other. FIG. 7 is a diagram illustrating a table indicating a relationship in which the three-dimensional information and the imaging mode according to the thickness of the breast are associated with each other. In tomosynthesis imaging, imaging is performed by irradiating the breast M with radiation at each of a plurality of radiation source positions. Thus, an angle of incidence of the radiation on the radiation detector 15 differs at each imaging position. For this reason, in a case where imaging is performed using a grid, vignetting in which the radiation is blocked by the grid occurs depending on the radiation source position, and as a result, an amount of the radiation reaching the radiation detector 15 may be reduced. Thus, in a case where tomosynthesis imaging is performed, the grid is not used.

On the other hand, in a case where the grid is not used, a noise in the projection image and even the tomographic image is increased due to an influence of the scattered radiation, and as a result, an image quality is deteriorated. In particular, in a case of a patient with a thick breast M, a degree of scattering of the radiation is increased, and this causes an increase of a noise caused by the scattered radiation. As a result, even though tomosynthesis imaging is performed, it may be more difficult to detect an abnormal portion as compared with a simple two-dimensional image.

Therefore, as illustrated in FIG. 7, in the table LUT2, in a case where the thickness of the breast M is equal to or smaller than a threshold value Th2, simple imaging is associated with the three-dimensional information which is equal to or smaller than a first threshold value Th1, and in a case where the thickness of the breast M is larger than the threshold value Th2, combination imaging of simple imaging and tomosynthesis imaging is associated with the three-dimensional information which is equal to or smaller than the first threshold value Th1. Further, in a case where the thickness of the breast is equal to or smaller than the threshold value Th2, tomosynthesis imaging is associated with the three-dimensional information which is larger than the first threshold value Th1, and in a case where the thickness of the breast M is larger than the threshold value Th2, combination imaging of simple imaging and tomosynthesis imaging is associated with the three-dimensional information which is larger than the first threshold value Th1. The first threshold value Th1 for the three-dimensional information is used in both FIGS. 6 and 7. On the other hand, different threshold values may be set in each of FIGS. 6 and 7. Further, the second threshold value may be set to a different value according to the type of the three-dimensional information.

The imaging mode setting unit 33 sets an imaging mode for the second imaging by referring to the table LUT1 or the table LUT2 based on the three-dimensional information derived by the three-dimensional information derivation unit 32 and the thickness of the breast M. That is, in a case where only the three-dimensional information is used, by referring to the table LUT1 illustrated in FIG. 6, the imaging mode setting unit 33 sets the imaging mode to simple imaging in a case where the three-dimensional information is equal to or smaller than the first threshold value Th1, and sets the imaging mode to tomosynthesis imaging in a case where the three-dimensional information is larger than the first threshold value Th1.

Further, in a case where the three-dimensional information and the thickness of the breast M are used, by referring to the table LUT2 illustrated in FIG. 7, in a state where the three-dimensional information is equal to or smaller than the first threshold value Th1, the imaging mode setting unit 33 sets the imaging mode to simple imaging in a case where the thickness of the breast M is equal to or smaller than the threshold value Th2, and sets the imaging mode to combination imaging in a case where the thickness of the breast M is larger than the threshold value Th2. Further, in a state where the three-dimensional information is larger than the first threshold value Th1, the imaging mode setting unit 33 sets the imaging mode to tomosynthesis imaging in a case where the thickness of the breast M is equal to or smaller than the second threshold value Th2, and sets the imaging mode to combination imaging in a case where the thickness of the breast M is larger than the second threshold value Th2.

The set imaging mode is output to the image acquisition unit 31. The image acquisition unit 31 acquires a second breast image by performing second imaging of the breast M according to the set imaging mode.

In a case where the imaging mode is simple imaging, the second breast image is a simple two-dimensional image. In a case where the imaging mode is tomosynthesis imaging, the second breast image is a tomographic image which is reconfigured using the projection images Gi acquired by tomosynthesis imaging. The reconfiguration will be described later. In a case where the imaging mode is combination imaging, the second breast image is a simple two-dimensional image and a tomographic image.

Figure 8:
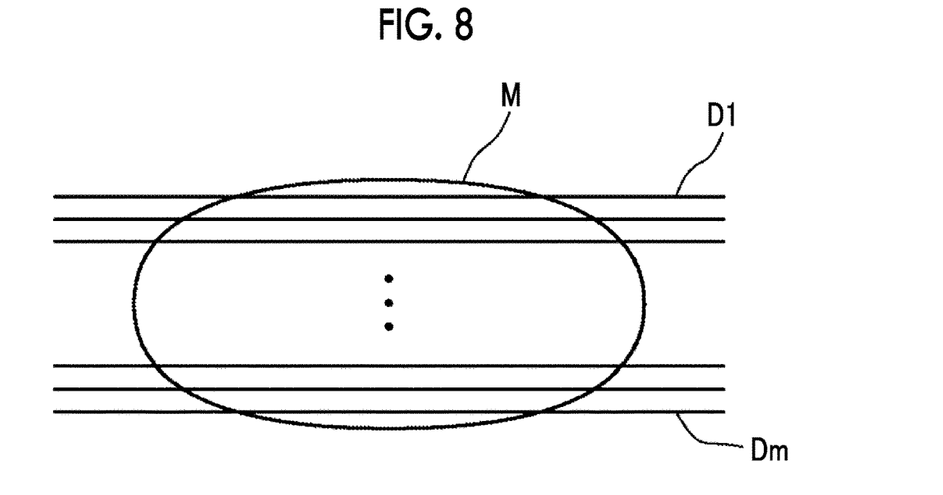
FIG. 8 is a diagram for explaining reconfiguration.

The reconfiguration unit 34 generates tomographic images in which the desired tomographic planes of the breast M are highlighted by reconfiguring the plurality of projection images Gi acquired by tomosynthesis imaging. Specifically, the reconfiguration unit 34 generates a plurality of tomographic images Dj (j=1 to m) on each of the plurality of tomographic planes of the breast M as illustrated in FIG. 8 by reconfiguring the plurality of projection images Gi using a known inverse projection method, such as a simple inverse projection method or a filtering inverse projection method. In this case, a three-dimensional coordinate position in a three-dimensional space including the breast M is set, pixel values at corresponding pixel positions in the plurality of projection images Gi are reconfigured with respect to the set three-dimensional coordinate position, and pixel values at the coordinate positions are calculated.

The display control unit 35 displays, on the display unit 3, the first breast image acquired by the first imaging and the second breast image acquired by the second imaging according to the imaging mode. In displaying of the second breast image, the display control unit 35 displays, on the display unit 3, a simple two-dimensional image in a case where the imaging mode is simple imaging. The display control unit 35 displays, on the display unit 3, a tomographic image in a case where the imaging mode is tomosynthesis imaging. The display control unit 35 displays, on the display unit 3, a simple two-dimensional image and a tomographic image in a case where the imaging mode is combination imaging.

Figure 9:
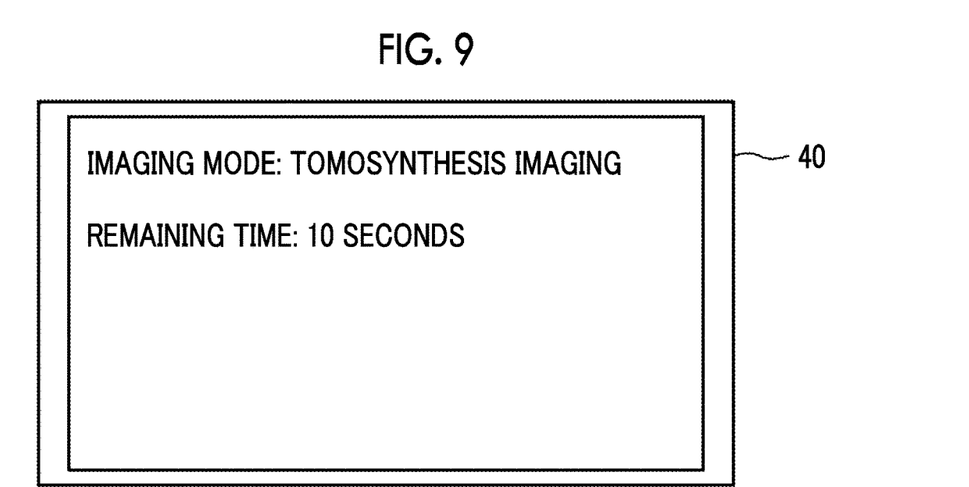
FIG. 9 is a diagram illustrating a notification displayed on a display unit.

In a case where the imaging mode is tomosynthesis imaging and in a case where the imaging mode is combination imaging, the notification unit 36 notifies the display unit 40 provided in the mammography apparatus 10 and the display unit 3 of at least one of the imaging mode or the remaining time of the second imaging so as to display the information. In the present embodiment, the notification unit 36 notifies the display unit 40 and the display unit 3 of both the imaging mode and the remaining time of the second imaging. FIG. 9 is a diagram illustrating a notification displayed on the display unit 40. As illustrated in FIG. 9, the display unit 40 displays "tomosynthesis imaging" as the imaging mode and "10 seconds" as the remaining time. The remaining time is counted down as the imaging progresses, and in a case where the second imaging is completed, the remaining time becomes 0. Further, the same notification is displayed on the display unit 3. Instead of a numerical value indicating the remaining time, a bar indicating the remaining time may be displayed.

In a case where the imaging mode is simple imaging, the notification unit 36 may notify the display unit 40 and the display unit 3 at least one of the imaging mode or the remaining time of the second imaging.

Figure 10:
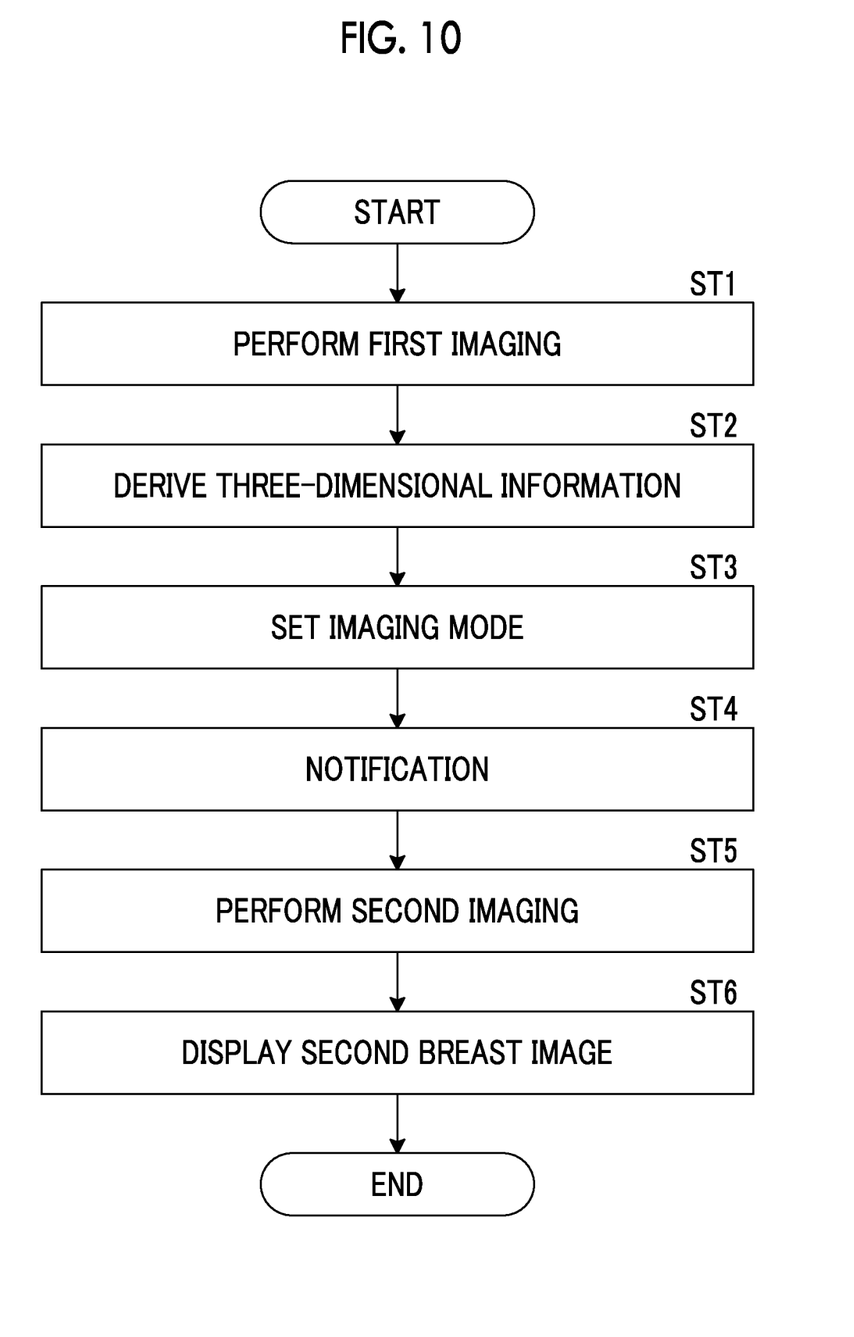
FIG. 10 is a flowchart illustrating processing performed in the present embodiment.

Next, processing performed in the present embodiment will be described. FIG. 10 is a flowchart illustrating processing performed in the present embodiment. It is assumed that the positioning of the breast M on the imaging table 13 is completed. In a case where the operator inputs an instruction for pre-imaging via the input unit 4, the processing is started. The image acquisition unit 31 acquire a first breast image MG1 by causing the mammography apparatus 10 to perform the first imaging (step ST1). At this time, a state where the imaging switch 5 is pressed by the operator is maintained until the second imaging is completed unless the positioning is performed again.

Next, the three-dimensional information derivation unit 32 derives three-dimensional information of the mammary gland included in the first breast image MG1 (step ST2). The imaging mode setting unit 33 sets an imaging mode for the second imaging of the breast M based on the three-dimensional information (step ST3). In addition, the notification unit 36 notifies the display unit 40 and the display unit 3 of the set imaging mode and the remaining time of the second imaging (step ST4). Further, the image acquisition unit 31 acquires a second breast image by performing second imaging based on the set imaging mode (step ST5). The display control unit 35 displays the second breast image on the display unit 3 (step ST6), and the process is ended. The operator can release the imaging switch 5 after confirming that the imaging is completed by looking at the notification by the notification unit 36.

In a state where the position of the radiation source 16 at the time of the first imaging is the reference radiation source position Sc, in a case where the imaging mode is set to simple imaging, the second imaging may be performed without moving the radiation source 16. In a state where the position of the radiation source 16 at the time of the first imaging is the reference radiation source position Sc, in a case where the imaging mode is set to tomosynthesis imaging, the second imaging may be performed after the radiation source 16 is moved to the radiation source position S1. In this case, while the radiation source 16 is moving, according to the first imaging condition, the filter and the target may be changed, and the grid 20 may be removed. In a state where the position of the radiation source 16 at the time of the first imaging is the reference radiation source position Sc, in a case where the imaging mode is set to combination imaging, the simple imaging may be performed first, the radiation source 16 may be moved to the radiation source position S1, and then the second imaging may be performed.

Further, in a state where the position of the radiation source 16 at the time of the first imaging is the radiation source position S1, in a case where the imaging mode is set to simple imaging, the second imaging may be performed after the radiation source 16 is moved to the reference radiation source position Sc. In this case, while the radiation source 16 is moving, according to the second imaging condition, the grid 20 may be inserted after the filter and the target are changed. In a state where the position of the radiation source 16 at the time of the first imaging is the radiation source position S1, in a case where the imaging mode is set to tomosynthesis imaging, the second imaging may be performed without moving the radiation source 16. In a state where the position of the radiation source 16 at the time of the first imaging is the radiation source position S1, in a case where the imaging mode is set to combination imaging, tomosynthesis imaging may be performed first, the radiation source 16 may be moved to the reference radiation source position Sc after the tomosynthesis imaging is completed, and then the second imaging may be performed.

As described above, in the present embodiment, the imaging mode for the second imaging of the breast M is set based on the three-dimensional information of the mammary gland included in the first breast image acquired by the first imaging, and the second breast image is acquired by imaging the breast with the same positioning as positioning of the first imaging by the second imaging based on the set imaging mode. Here, the three-dimensional information of the mammary gland includes not only information of the breast image in an expansion direction but also information of the breast in a thickness direction at the time of imaging. Thereby, the three-dimensional information of the mammary gland more clearly represents a distribution of the mammary gland included in the breast M. Therefore, according to the present embodiment, it is possible to appropriately set the imaging mode of the breast M.

Further, by setting the imaging mode based on the thickness of the breast M, it is possible to more appropriately set the imaging mode.

Here, in the mammography apparatus 10, since the breast M is compressed for imaging, a burden on a patient is heavy. For this reason, in a case where a patient does not know what kind of imaging is currently being performed, the patient cannot know how long the breast M will be compressed. As a result, the patient may feel anxiety. Further, in a case where the operator releases the imaging switch 5 before the imaging is completed, the imaging is stopped. For this reason, the operator cannot release the imaging switch 5 during the imaging. On the other hand, in a case where the operator does not know a timing when the imaging is completed, the operator cannot know how long the imaging switch 5 should be pressed.

In the present embodiment, the notification unit 36 notifies the display unit 40 and the display unit 3 of the set imaging mode and the remaining time of the second imaging. Thereby, the patient can know the current imaging mode and the time until the imaging is completed. Therefore, it is possible to reduce anxiety of the patient. Further, since the operator who performs imaging can know a timing when the imaging is completed by the notification, the operator can release the imaging switch 5 without anxiety.

In the embodiment, the radiation is not particularly limited. For example, α-rays or γ-rays other than X-rays may be applied.

Further, in the embodiment, the notification unit 36 causes the display unit 3 and the display unit 40 to display the notification. On the other hand, the present disclosure is not limited thereto. The notification unit 36 may cause the display unit 3 or the display unit 40 to display the notification. Further, the display may be changed, or in addition to the display, a sound notification may be output.

Further, in the embodiment, for example, the following various processors may be used as a hardware structure of processing units performing various processing, such as the image acquisition unit 31, the three-dimensional information derivation unit 32, the imaging mode setting unit 33, the reconfiguration unit 34, the display control unit 35, and the notification unit 36. The various processors include, as described above, a CPU, which is a general-purpose processor that functions as various processing units by executing software (program), and a dedicated electric circuit, which is a processor having a circuit configuration specifically designed to execute a specific processing, such as a programmable logic device (PLD) or an application specific integrated circuit (ASIC) that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. As described above, the various processing units are configured by using one or more various processors as a hardware structure.

Further, as the hardware structure of the various processors, more specifically, an electric circuit (circuitry) in which circuit elements such as semiconductor elements are combined may be used.

What is claimed is:

1. An imaging control apparatus comprising at least one processor, wherein the processor is configured to:
    acquire a first breast image by imaging a breast which is being compressed by first imaging;
    derive three-dimensional information of a mammary gland included in the first breast image; and
    set an imaging mode for second imaging of the breast based on the three-dimensional information,
    acquire a second breast image by imaging the breast without releasing a state during the first imaging where the breast is compressed by the second imaging based on the set imaging mode.

2. The imaging control apparatus according to claim 1, wherein the processor is configured to derive, as the three-dimensional information, any of a volume of the mammary gland, a ratio of the volume of the mammary gland, or a thickness of the mammary gland in an interest region of the breast.

3. The imaging control apparatus according to claim 2, wherein the interest region is an entire region of the breast.

4. The imaging control apparatus according to claim 2, wherein the interest region is a region in which the mammary gland exists in a predetermined ratio or more with respect to a thickness of the breast.

5. The imaging control apparatus according to claim 1, wherein the processor is configured to set, as the imaging mode, any of simple two-dimensional imaging, tomosynthesis imaging, and combination imaging of simple imaging and tomosynthesis imaging based on the three-dimensional information.

6. The imaging control apparatus according to claim 5, wherein the processor is configured to set the imaging mode based on a thickness of the breast.

7. The imaging control apparatus according to claim 5, wherein the processor is configured to set the imaging mode to the simple two-dimensional imaging in a case where the volume of the mammary gland or the ratio of the volume of the mammary gland is equal to or smaller than a predetermined threshold value, and sets the imaging mode to the tomosynthesis imaging in a case where the volume of the mammary gland or the ratio of the volume of the mammary gland is larger than the threshold value.

8. The imaging control apparatus according to claim 6, wherein the processor is configured to set the imaging mode to the simple two-dimensional imaging in a case where the volume of the mammary gland or the ratio of the volume of the mammary gland is equal to or smaller than a predetermined first threshold value and the thickness of the breast is equal to or smaller than a predetermined second threshold value, sets the imaging mode to the tomosynthesis imaging in a case where the volume of the mammary gland or the ratio of the volume of the mammary gland is larger than the first threshold value and the thickness of the breast is equal to or smaller than the second threshold value, and sets the imaging mode to the combination imaging in a case where the thickness of the breast is larger than the second threshold value.

9. The imaging control apparatus according to claim 5, wherein the processor is configured to set the imaging mode to the simple two-dimensional imaging in a case where the thickness of the mammary gland is equal to or smaller than a predetermined threshold value, and sets the imaging mode to the tomosynthesis imaging in a case where the thickness of the mammary gland is larger than the threshold value.

10. The imaging control apparatus according to claim 6, wherein the processor is configured to set the imaging mode to the simple two-dimensional imaging in a case where the thickness of the mammary gland is equal to or smaller than a predetermined third threshold value and the thickness of the breast is equal to or smaller than a predetermined fourth threshold value, sets the imaging mode to the tomosynthesis imaging in a case where the thickness of the mammary gland is larger than the third threshold value and the thickness of the breast is equal to or smaller than the fourth threshold value, and sets the imaging mode to the combination imaging in a case where the thickness of the breast is larger than the fourth threshold value.

11. The imaging control apparatus according to claim 1 wherein the processor is configured to notify at least one of the set imaging mode or a remaining time of the second imaging by the imaging mode.

12. An imaging control method comprising:
    acquiring a first breast image by imaging a breast which is being compressed by first imaging;
    deriving three-dimensional information of a mammary gland included in the first breast image;
    setting an imaging mode for second imaging of the breast based on the three-dimensional information; and
    acquiring a second breast image by imaging the breast without releasing a state during the first imaging where the breast is compressed by the second imaging based on the set imaging mode.

13. A non-transitory computer-readable storage medium that stores an imaging control program causing a computer to execute:
- a procedure of acquiring a first breast image by imaging a breast which is being compressed by first imaging;
- a procedure of deriving three-dimensional information of a mammary gland included in the first breast image;
- a procedure of setting an imaging mode for second imaging of the breast based on the three-dimensional information; and
- a procedure of acquiring a second breast image by imaging the breast without releasing a state during the first imaging where the breast is compressed by the second imaging based on the set imaging mode.

* * * * *